US012329629B2

(12) United States Patent
Walsh et al.

(10) Patent No.: US 12,329,629 B2
(45) Date of Patent: Jun. 17, 2025

(54) ADDITIVE MANUFACTURING OF POROUS COATINGS SEPARATE FROM SUBSTRATE

(71) Applicant: Howmedica Osteonics Corp., Mahwah, NJ (US)

(72) Inventors: Gearoid Walsh, Ennis (IE); Lewis Mullen, Englewood, NJ (US); John Scanlan, Limerick (IE); Robert W. Klein, Orangeburg, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 17/830,071

(22) Filed: Jun. 1, 2022

(65) Prior Publication Data

US 2022/0387163 A1 Dec. 8, 2022

Related U.S. Application Data

(60) Provisional application No. 63/208,242, filed on Jun. 8, 2021.

(51) Int. Cl.
*A61F 2/02* (2006.01)
*B22F 3/00* (2021.01)
(Continued)

(52) U.S. Cl.
CPC ............. *A61F 2/02* (2013.01); *B22F 3/004* (2013.01); *B22F 3/02* (2013.01); *B22F 3/10* (2013.01);
(Continued)

(58) Field of Classification Search
CPC .... A61F 2/02; A61F 2210/0076; A61F 2/389; A61F 2002/30769; A61F 2002/3092;
(Continued)

(56) References Cited

U.S. PATENT DOCUMENTS 4,550,448 A 11/1985 Kenna
4,612,160 A 9/1986 Donlevy et al.
(Continued)

FOREIGN PATENT DOCUMENTS

CN 109158730 A 1/2019
WO 2013116736 A1 8/2013
(Continued)

OTHER PUBLICATIONS

ASM Glossary of Metallurgical and Metalworking Terms, Metals Handbook Desk Edition, Second Edition, J.R. Davis, Editor, p. 3-63, 1998 (Year: 1998).*
(Continued)

*Primary Examiner* — Rebecca Janssen
(74) *Attorney, Agent, or Firm* — Lerner David LLP

(57) ABSTRACT

An implant is produced by fabricating first and second layers. The first layer of repeated and truncated building units is fused together to define pores. The second layer of repeated and truncated building units are fused together to define pores and fused onto the first layer of truncated building units. The first and the second layers form at least part of a porous portion of the implant. The formed porous portion is attached onto a base portion of an implant. The truncated building units of each of the first and the second layers are in the form of spatially overlapping three-dimensional shapes.

21 Claims, 9 Drawing Sheets

(51) Int. Cl.
| | |
|---|---|
| *B22F 3/02* | (2006.01) |
| *B22F 3/10* | (2006.01) |
| *B22F 3/12* | (2006.01) |
| *B22F 10/10* | (2021.01) |
| *B22F 10/14* | (2021.01) |
| *B33Y 10/00* | (2015.01) |
| *B22F 10/20* | (2021.01) |
| *B33Y 80/00* | (2015.01) |

(52) U.S. Cl.
CPC ............... *B22F 3/12* (2013.01); *B22F 10/10* (2021.01); *B22F 10/14* (2021.01); *A61F 2210/0076* (2013.01); *B22F 10/20* (2021.01); *B33Y 10/00* (2014.12); *B33Y 80/00* (2014.12)

(58) Field of Classification Search
CPC .. A61F 2002/30948; A61F 2002/30952; A61F 2002/30957; A61F 2002/30968; A61F 2002/3097; A61F 2002/30985; A61F 2/3094; A61F 2/30942; B22F 3/004; B22F 3/02; B22F 3/10; B22F 3/12; B22F 10/10; B22F 10/14; B22F 10/20; B22F 3/1121; B22F 5/00; B22F 7/002; B22F 3/225; B33Y 10/00; B33Y 80/00; A61L 27/04; A61L 27/56
See application file for complete search history.

(56) References Cited

U.S. PATENT DOCUMENTS

| | | | |
|---|---|---|---|
| 5,358,533 | A | 10/1994 | Noiles et al. |
| 5,405,389 | A | 4/1995 | Conta et al. |
| 5,524,695 | A | 6/1996 | Schwartz |
| 6,179,876 | B1 | 1/2001 | Stamper et al. |
| 7,001,672 | B2 | 2/2006 | Justin et al. |
| 7,537,664 | B2 | 5/2009 | O'Neill et al. |
| 7,674,426 | B2 | 3/2010 | Grohowski, Jr. |
| 8,070,821 | B2 | 12/2011 | Roger |
| 8,350,186 | B2 | 1/2013 | Jones et al. |
| 8,748,855 | B2 | 6/2014 | Appleby et al. |
| 8,828,311 | B2 | 9/2014 | Medina et al. |
| 8,852,359 | B2 | 10/2014 | Walker et al. |
| 8,985,430 | B2 | 3/2015 | Charlebois et al. |
| 9,089,427 | B2 | 7/2015 | Grohowski, Jr. |
| 9,180,010 | B2 | 11/2015 | Dong et al. |
| 9,370,609 | B2 | 6/2016 | Grohowski, Jr. |
| 9,606,054 | B2 | 3/2017 | King et al. |
| 9,901,451 | B2 | 2/2018 | Conway et al. |
| 10,065,396 | B2 | 9/2018 | Verreault et al. |
| 10,456,833 | B2 | 10/2019 | Gibson et al. |
| 10,525,688 | B2 | 1/2020 | O'Neill et al. |
| 10,596,660 | B2 | 3/2020 | McCarthy et al. |
| 10,688,718 | B2 | 6/2020 | Wieber et al. |
| 10,888,362 | B2 | 1/2021 | Swarts |
| 2010/0094420 | A1* | 4/2010 | Grohowski, Jr. ......... B22F 3/16 623/16.11 |
| 2011/0160867 | A1* | 6/2011 | Meridew ............ A61B 17/1659 29/428 |
| 2012/0232654 | A1* | 9/2012 | Sharp .................... B33Y 10/00 29/428 |
| 2014/0195001 | A1 | 7/2014 | Grohowski, Jr. |
| 2018/0333780 | A1* | 11/2018 | Klein .................... B22F 3/1115 |
| 2018/0344468 | A1 | 12/2018 | Landon |
| 2019/0047216 | A1 | 2/2019 | Emamjomeh et al. |
| 2019/0193159 | A1 | 6/2019 | Gibson et al. |
| 2019/0351620 | A1 | 11/2019 | Jaiswal et al. |
| 2020/0360996 | A1 | 11/2020 | Woestmann et al. |
| 2020/0368970 | A1 | 11/2020 | Georgeson et al. |
| 2021/0316367 | A1* | 10/2021 | Padilla .................. B33Y 50/00 |
| 2022/0184276 | A1* | 6/2022 | Liu ........................ B33Y 80/00 |

FOREIGN PATENT DOCUMENTS

| | | |
|---|---|---|
| WO | 2018112263 A1 | 6/2018 |
| WO | 2019241117 A1 | 12/2019 |
| WO | 2020006237 A1 | 1/2020 |
| WO | 2021021084 A1 | 2/2021 |

OTHER PUBLICATIONS

Partial European Search Report issued in Appln. No. 22177721.2 dated Oct. 27, 2022 (16 pages).

Muth et al., Novel Highly Porous Metal Technology in Artificial Hip and Knee Replacement: Processing Methodologies and Clinical Applications, JOM, Published online Dec. 27, 2012, pp. 318-325, vol. 65, No. 2.

Depuy Synthes, Gription Pourous Coating, Product Rationale, Issued Jul. 2017, 16 pages.

Stryker, GMRS Distal Femur Global Modular Replacment System, 2018, 48 pages.

Stryker, Triathlon Titanium Total Knee Arthroplasty with Triathlon Cementless beaded Peri-Apatite (PA) femoral component, 2019, 72 pages.

* cited by examiner

ADDITIVE MANUFACTURING OF POROUS COATINGS SEPARATE FROM SUBSTRATE

CROSS-REFERENCE TO RELATED APPLICATIONS

The present application claims the benefit of the filing date of U.S. Provisional Patent Application No. 63/208,242 filed Jun. 8, 2021, the disclosure of which is hereby incorporated herein by reference.

BACKGROUND

Some varieties of orthopedic implants act as prostheses replacing a removed portion of bone. For example, where a portion of a bone is injured or diseased, such portion may be removed and replaced by an implant of similar size and shape. Such implants may benefit from having hard, smooth outward facing surfaces, particularly where the removed portion of the bone forms part of a joint. However, smooth surfaces tend not to be conducive to fixation of the implant into the bone. Implants may therefore be provided with a rough or porous side for contacting the cut surface of the bone to facilitate growth of the bone into the implant.

To allow for a porous side, an implant may be formed in a near complete shape with a recess for accepting porous material. The recess may then be filled with the porous material, such as, for example, layers of beads and a strong adhesive to bind the beads together as well as to bind the layers of beads into the recess. Known processes for filling recesses with such material tend to be painstaking and time consuming, therefore limiting a rate at which implants can be manufactured. Implant manufacture could be accelerated and potentially made more economical if porous or rough sides for implants could be created more efficiently.

BRIEF SUMMARY

According to some aspects, a porous portion for an orthopedic implant may be fabricated as a unit separated from a body of the implant. The porous portion may be fabricated through additive manufacturing. The porous portion may include a structure such as multiple layers of beads. Beads in a layer of beads on a side of the porous portion intended to contact the body of the implant may each have a planar surface, and the planar surfaces of the beads may be coplanar so as to collectively provide a planar surface for placement upon the body of the implant. The beads in the layer of beads on the side of the porous portion intended to contact the body of the implant may also or in the alternative include either one or both of indentations and pegs to further facilitate securement of the porous portion onto the body of the implant.

In further aspects, a printing plan for additively manufacturing a porous portion may be generated by a computer, e.g., by using a computer-aided design or modeling program, from a digitized repeatable unit cell structure and a digitized computer-aided design (CAD) volume corresponding to an overall shape of the porous portion. The unit cell structure may be tessellated throughout the digitized CAD volume. The tessellated set of unit cells may then be subdivided into digitized slices corresponding to deposit able layers, and the digitized slices may be used to create a printing path and a series of instructions stored in a component file readable by a computer-readable storage medium by which an additive manufacturing system may fabricate the porous portion.

In further aspects, a porous portion of an object may be placed in a cavity defined between two mold components before the cavity is filled in a metal injection molding (MIM) process to form a solid body portion of the object, which in some arrangements may be a medical implant. The porous portion may be placed upon a first of the two mold components before a second of the mold components is placed over the first mold component to create the cavity. The cavity may then be filled during the MIM process while the porous portion is received in the cavity. The porous portion may be trapped in the cavity while in a green state during the MIM process. A fully green state part may therefore result when the cavity is filled and the MIM process completed. The fully green state part may then be sintered in a single step such that the porous portion and the solid body portion of the object may both shrink.

According to another aspect, an implant may be produced by a process. In this process, a first layer of repeated and truncated building units may be fabricated. The repeated and truncated building units of the first layer may be fused together to define pores. A second layer of repeated and truncated building units may be fabricated. The repeated and truncated building units of the second layer may be fused together to define pores and may be fused onto the first layer of repeated and truncated building units. In this manner, the first and the second layers may form at least part of a porous portion of the implant. In some arrangements, the formed porous portion may be attached to a base portion of the implant. In some arrangements, the repeated and truncated building units of each of the first layer and the second layer may be in the form of spatially overlapping three-dimensional shapes, e.g., ellipses or polygons.

In another arrangement according to any of the foregoing, the building units of the first layer may be fused in a first repeating pattern, and the building units of the second layer may be fused in a second repeating pattern.

In another arrangement according to any of the foregoing, the building units of the first and the second layers may have the same size and shape, and first and the second repeating patterns may be the same pattern.

In another arrangement according to any of the foregoing, the building units of the first and the second layers may be tessellated.

In another arrangement according to any of the foregoing, at least some of the building units in the first layer may include an indentation extending inwardly from the flat bottom surface.

In another arrangement according to any of the foregoing, at least some of the building units in the first layer may include a stud extending away from the flat bottom surface.

In another arrangement according to any of the foregoing, building units defining a flat bottom surface extending over the entirety of the first layer may be fabricated during the fabrication of the first layer and thereby fabricate a flat bottom surface of the formed porous portion upon formation of the formed porous portion. In some such arrangements, the formed porous portion may be attached to a flat surface of the base of the implant during the attachment of the formed porous portion to the base of the implant.

In another arrangement according to any of the foregoing, the building units of the first layer may have a first volume, and the building units of the second layer may have a second volume different from the first volume.

In another arrangement according to any of the foregoing, a unit cell containing a geometry of the building units and a shape and size of the porous portion may be retrieved, by a processor, from a non-transitory computer readable medium on which the shape and size of the porous portion is stored in a separate location from the unit cell.

In another arrangement according to any of the foregoing, tessellated unit cells may be generated, by a processor, throughout a volume of a computer model derived from the shape and size of the porous portion. In some such arrangements, the tessellated unit cells within the computer model may be filled with digitized bead portions. Each of the digitized bead portions may correspond to a plurality of beads. In some such arrangements, the plurality of beads may be fabricated during the fabrication of each of the first and the second layers of the implant.

In another arrangement according to any of the foregoing, a third layer of the implant may be fabricated. In fabricating the third layer, additional beads may be fused onto the second layer such that the third layer forms at least a portion of the porous portion of the implant. The beads in the second layer may be different from the beads in the first layer, and the beads in the third layer may be different from the beads in the first layer and the beads in the second layer. A third layer, a fourth layer, a fifth layer, or any number of additional layers may also be fabricated by fusion of beads onto earlier layers.

In another arrangement according to any of the foregoing, the building units in the third layer may have a volume that is different than a volume of the building units in the first layer, and the building units in the second layer may have a volume that is between the volume of the building units in the first layer and the volume of the building units in the third layer.

In another arrangement according to any of the foregoing, the implant may be a patient-specific implant.

In another arrangement according to any of the foregoing, the patient-specific implant may correspond to a three-dimensional computer-aided design (CAD) model based on a computerized tomography (CT) scan or a magnetic resonance imaging (MRI) scan.

In another arrangement according to any of the foregoing, the implant may be a femoral implant, a knee implant, a hip implant, a spinal implant, a shoulder implant, a finger implant, a toe implant, a foot implant, a wrist implant, an ankle implant, a mandibular implant, or a cranial implant.

In another aspect, a medical implant may be manufactured by a process. In this process, a prefabricated porous component may be placed on a supporting region of a first mold component. A second mold component may be positioned adjacent to the first mold component such that a cavity in the form of a base of the implant is formed between the first mold component and the second mold component. While the prefabricated component is placed on the supporting region, the cavity may be filled with a metal powder mixture to form the implant.

In another arrangement according to any of the foregoing, the metal powder mixture may be a metal injection molding feedstock.

In another arrangement according to any of the foregoing, the prefabricated component may be made of a same material as the metal powder mixture.

In another arrangement according to any of the foregoing, the prefabricated component may comprise studs extending outward from other surfaces of the prefabricated component. In some such arrangements, the prefabricated component and the second mold component may be positioned such that the studs extend into the cavity and are over molded by the metal powder mixture upon filling the cavity.

In another arrangement according to any of the foregoing, the metal powder mixture may be compacted to provide a solidified base formed on the prefabricated component such that the solidified base and the prefabricated component form at least a first portion of the implant. The first portion of the implant may be finished to a state in which the prefabricated component contains more voids per unit volume than the solidified base.

In some such arrangements, the first portion of the implant may be heated during its finishing to remove a filler from the metal powder mixture.

In another arrangement according to any of the foregoing, the prefabricated component may remain in a green state until the finishing of the first portion of the implant.

In another arrangement according to any of the foregoing, a supporting region of a surface of the first mold component may be part of a convex portion of the first mold component.

In another arrangement according to any of the foregoing, the second mold component may include a concave portion, and boundaries of the cavity corresponding to exterior contours of the medical implant may be defined at least partially by the convex portion of the first mold component and the concave portion of the second mold component.

In another arrangement according to any of the foregoing, the implant may be a patient-specific implant.

In another arrangement according to any of the foregoing, the patient-specific implant may correspond to a three-dimensional CAD model based on a CT scan or an MRI scan.

In another arrangement according to any of the foregoing, the implant may be a femoral implant, a knee implant, a hip implant, a spinal implant, a shoulder implant, a finger implant, a toe implant, a foot implant, a wrist implant, an ankle implant, or a cranial implant.

In another aspect, a medical implant may be produced by a process. In this process, a first green state component may be additively manufactured by binding first metal particles with a binder, metal injection molding a second green state component, and sintering the first green state component and the second green state component together to form at least a first portion of the medical implant. In this manner, the first portion of the medical implant may include joined sintered forms of the first green state component and the second green state component.

In another arrangement according to any of the foregoing, the sintered forms of the first green state component and the second green state component may be in the form of a first sintered component and a second sintered component, respectively, and the first sintered component may contain more voids per unit volume than the second sintered component.

In another arrangement according to any of the foregoing, the first sintered component may be porous, and the second sintered component may be solid.

In another arrangement according to any of the foregoing, the first green state component may have a volume that is approximately 20% greater than a volume of the first sintered component.

In another arrangement according to any of the foregoing, the second green state component may have a volume that is approximately 20% greater than a volume of the second sintered component.

In another arrangement according to any of the foregoing, feedstock may be injected into a cavity containing the first green state component during the metal injection molding such that the first green state component and second green state component are joined as a green body.

In another aspect, a green state medical implant may comprise a first component and a second component. The first component may include metal particles and a binder binding the metal particles. The second component may include the metal particles and the binder binding the metal particles. The second component may be assembled but not fused to the first component.

In another arrangement according to any of the foregoing, the first component may be porous.

In another arrangement according to any of the foregoing, the second component may include a volume of binder per unit volume that exceeds a volume of binder per unit volume of the first component.

In another arrangement according to any of the foregoing, the filler may be plastic.

In another arrangement according to any of the foregoing, the first component may include a planar surface for interface with a resection surface of a bone, and the second component may include an exterior contour shaped to functionally replace an exterior contour of a resected portion of bone.

In another arrangement according to any of the foregoing, the implant may be a bone prosthesis.

In another aspect, a finished medical implant may be produced from the green state medical implant of any of the foregoing examples.

DETAILED DESCRIPTION

Figure 1A:
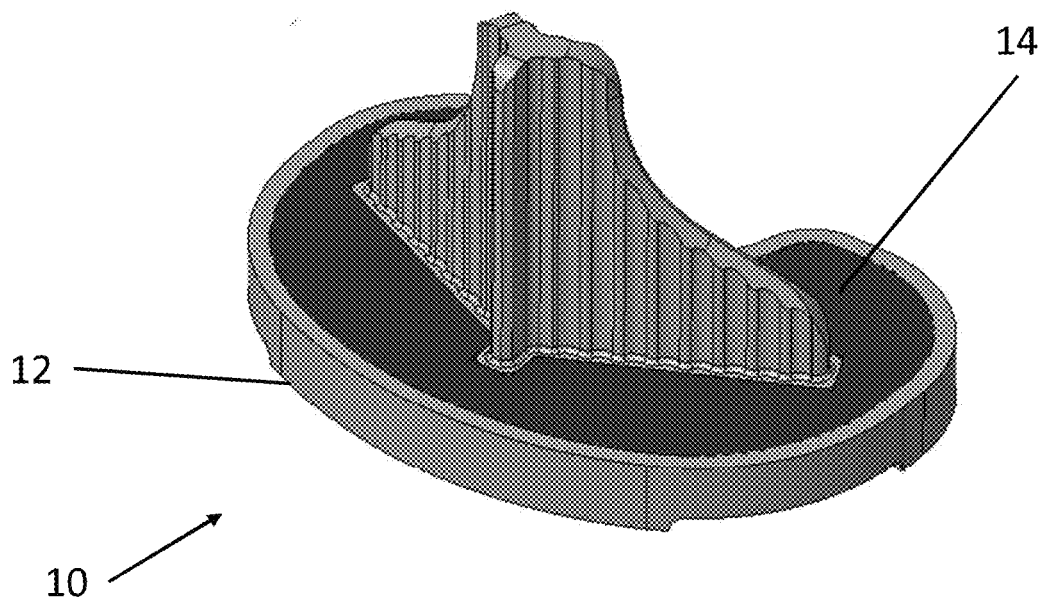
FIG. 1A is a perspective view of a medical implant according to an example.
Figure 1B:
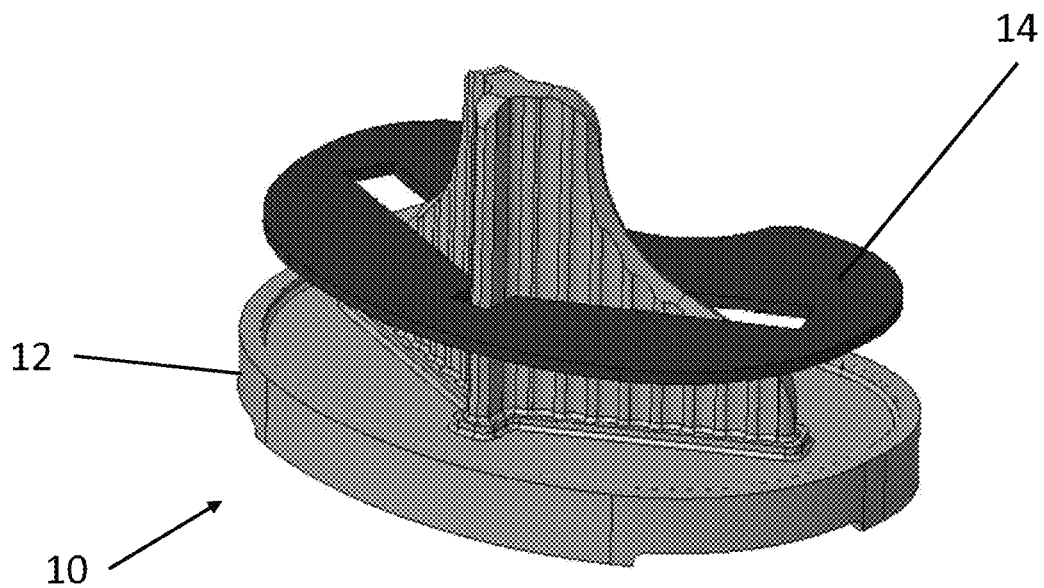
FIG. 1B is an exploded view of the implant of FIG. 1A in a pre-assembled state.

Referring now to FIG. 1A, implant 10 is a proximal tibial implant, but the teachings of this disclosure are applicable to at least any object having a porous first portion and a second portion, e.g., a solid portion, to be attached to the first portion of the object. As such, the present disclosure is especially applicable to implants prepared for placement against a resected surface of a bone. Implant 10 includes a body 12 acting as a base of the implant and a porous portion 14 acting as an interface for the implant and the bone. Porous portion 14 is configured to facilitate in-growth of bone such as when placed against a resection surface of a bone. As shown in FIG. 1B, porous portion 14 may be formed as a separate component from that of body 12 but may be joined to body 12 as shown in FIG. 1A such that bone in-growth into porous portion 14 acts to secure implant 10 as a whole, and thus body 12, to the bone. Both body 12 and porous portion 14 preferably may be made of the same metal of various metals such as titanium, titanium alloys, stainless steel, cobalt chrome alloys, tantalum and niobium, or any combination thereof. Porous portion 14 may be joined to body 12 by an adhesive, e.g., fish glue, sintering or other appropriate joining process known to those skilled in the art.

Body 12 may be fabricated by a number of processes, some of which are discussed further herein. In some arrangements, body 12 may be die cast and later machined, such as using a computer-aided manufacturing (CAM) process. In some arrangements, body 12 may be formed by an additive manufacturing process, including but not limited to electron beam melting (EBM), selective laser sintering (SLS), and selective laser melting (SLM), and blown powder fusion for use with metal powders.

Figure 1C:
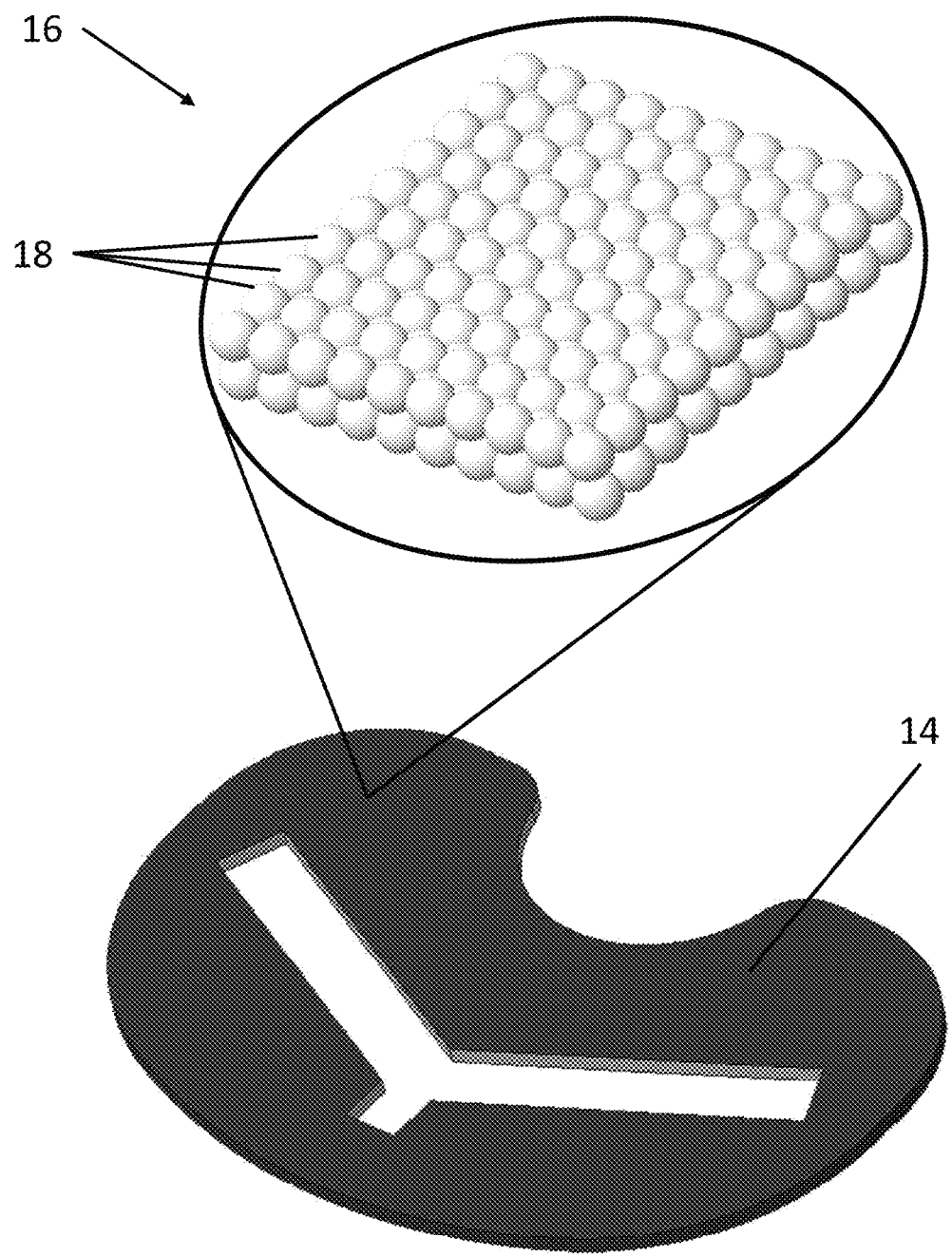
FIG. 1C is a perspective view of a porous portion of the implant of FIG. 1A and an expanded view of a segment of the porous portion.

As shown in FIG. 1C, in some arrangements, a porous beaded structure 16 that forms porous portion 14 may be constituted of a repeating pattern of building units. In the illustrated example, the building units are beads 18 adhered or otherwise joined to one another. Beads 18 of the illustrated example are spherical, though the teachings of the present disclosure are applicable with beads of any shape, such as, for example, polyhedral beads.

In some arrangements, porous portion 14 may be formed by an additive manufacturing process, e.g., EBM, SLM, SLS, or a binder jetting process. In some arrangements, porous portion 14 may be in the form of porous beaded structure 16. In some arrangements, porous portion 14 may be in the form of overlapping lines of solidified powder as disclosed in U.S. Pat. No. 7,537,664, the disclosure of which is hereby incorporated by reference herein. In some arrangements, porous portion 14 may be in the form of cellular structures defined by repeating formed porous geometries corresponding to digitized unit cells as disclosed in U.S. Pat. Nos. 10,525,688 and 9,180,010, the disclosures of which are hereby incorporated by reference herein. In some arrangements, porous portion 14 may be in the form of a mesh or chainmail as disclosed in U.S. Pat. Nos. 10,596,660 and 10,888,362, the disclosures of which are hereby incorporated by reference herein as if fully set forth herein.

When fabricating porous portion 14 by EBM, SLM, or SLS, a first layer or portion of a layer of metal powder is deposited onto a substrate and then scanned with a high energy beam so as to sinter or melt the powder and create a portion of a plurality of predetermined physical porous geometries. Successive layers of the metal powder are then deposited onto previous layers of the metal powder and also respectively scanned with the high energy beam prior to the deposition of subsequent layers of the metal powder. The scanning and depositing of successive layers of the metal powder continues the building process of the predetermined physical porous geometries. Such continuation of the building process refers not only to a continuation of a predetermined physical porous geometry from a previous layer but also a beginning of a new predetermined physical porous geometry as well as or instead of the completion of a predetermined physical porous geometry, depending on the desired characteristics of the structure to be fabricated.

The structures formed using this process may be partially porous and, if desired, have interconnecting pores to provide an interconnecting porosity. In some arrangements, the physical porous geometries may be defined by physical struts connected at vertices corresponding to digitized nodes within a computer-aided design or modeling program. The metal powder and thus the additively printed porous portion preferably may be made of any one or any combination of cobalt chrome alloy, titanium or alloy, stainless steel, niobium and tantalum. Thus, a mixture of desired mixed materials may be employed.

The high energy beam preferably may be an electron beam (e-beam) or laser beam and may be applied continuously to the powder or pulsed at a predetermined frequency. In some arrangements, the use of a laser or e-beam melting process may preclude the requirement for subsequent heat treatment of the structure fabricated by the additive manufacturing process, thereby preserving the initial mechanical properties of the additively manufactured porous portion. The high energy beam is emitted from a beam-generating apparatus to heat the metal powder sufficiently to sinter and preferably to at least partially melt or melt the metal powder. High energy beam generation equipment for manufacturing such structures may be one of many currently available including the "Concept laser M2 Cusing" machines, 200W M2 Cusing (series 3), kW M2 Cusing (Series 3), Dual kW M2 Cusing (Series 5) MCP REALIZER, the EOS M270, TRUMPF TRUMAFORM 250, the ARCAM EBM S12 and Q10 machine, and the like. The beam generation equipment may also be a custom-produced laboratory device.

The pore density, pore size and pore size distribution may be controlled from one location of the porous portion 14 to another. It is important to note that successive powder layers may differ in porosity by varying factors used for laser scanning powder layers. Additionally, the porosity of successive layers of powder may be varied by either creating a specific type of unit cell or manipulating various dimensions of a given unit cell. In some arrangements, the porosity may be a gradient porosity throughout at least a portion of the fabricated structure. The beam generation equipment may be programmed to proceed in a random generated manner to produce an irregular porous construct but with a defined level of porosity. Pseudo-random geometries may be formed by applying a perturbation to the vertices of porous geometries when preparing model build structures corresponding to the 3D structure to be fabricated. In this manner, the physical porous geometries may be randomized.

Referring now to FIGS. 2A-3B, unique various porous beaded structures may be used to form porous portion 14. Such beaded structure may be formed using additive manufacturing. Layers of material may be deposited to gradually construct the beads forming these beaded structures.

Figure 2A:
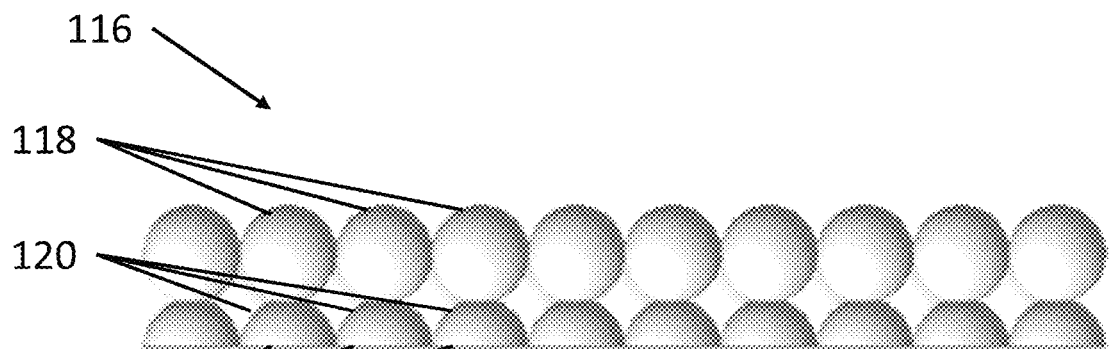
FIGS. 2A-2C illustrate various examples of edge portions of structures of which the porous portion of FIG. 1C may be made.

As shown in FIG. 2A, beaded structure 116 includes multiple layers of beads. One layer of whole beads 118 is illustrated, though a complete porous portion 14 may include several more. A layer of planed beads 120 is joined to the layer of whole beads 118. Each planed bead 120 includes a planar surface 122, and all planar surfaces 122 of planed beads 120 are coplanar with one another. Planed surfaces 122 thus collectively form a planar side of porous portion 14 which can facilitate secure attachment of porous portion 14 to body 12. Attachment of porous portion 14 to body 12 may be accomplished by, for example, adhesion with any suitable binder, such as fish glue.

In the illustrated example, each planed bead 120 is a frustum of the shape of whole beads 118. Thus, each planed bead is identical to whole beads 118 except for the respective planar surface 122 which truncates the planed bead 120. Moreover, the layer of planed beads 120 is constructed according to a repeating pattern that is identical to a repeating pattern according to which the layer of whole beads 118 is constructed, except that the portion of the pattern beyond planar surfaces 122 is not constructed.

Figure 2B:
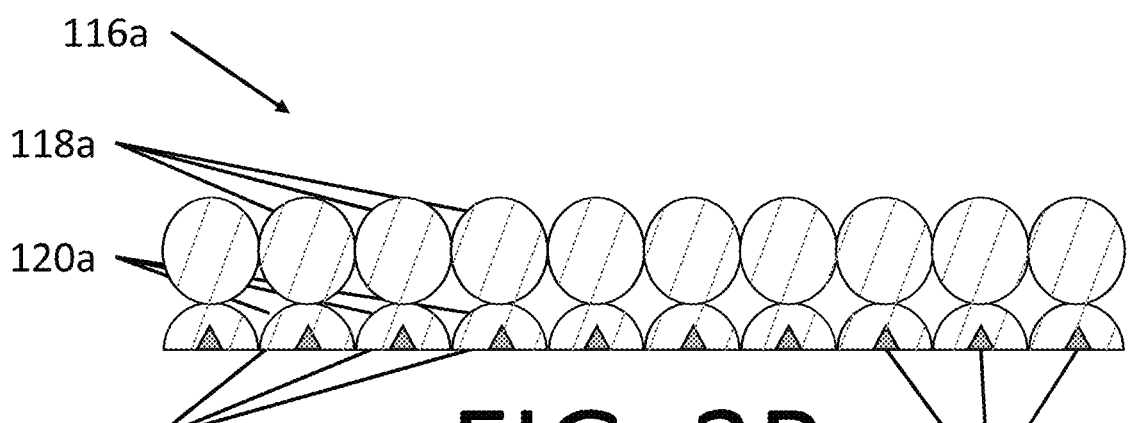

As shown in FIG. 2B, similar to structure 116 of FIG. 2A, beaded structure 116a includes a layer of whole beads 118a joined to a layer of planed beads 120a. However, in beaded structure 116a, planed beads 120a each include an indentation 124 extending inward from planar surface 122a. Indentations 124 may be in any shape, such as being conical as shown in the illustrated example. Moreover, indentations 124 may be provided in any quantity and at any respective locations relative to their respective planar surface 122a, though each indentation is present only in the center of the respective planar surface in the illustrated example. Indentations 124 may facilitate entry of a flowable adhesive, e.g., fish glue, into and engagement with beaded structure 116a, thus improving attachment of porous portion 14 to body 12.

Figure 2C:
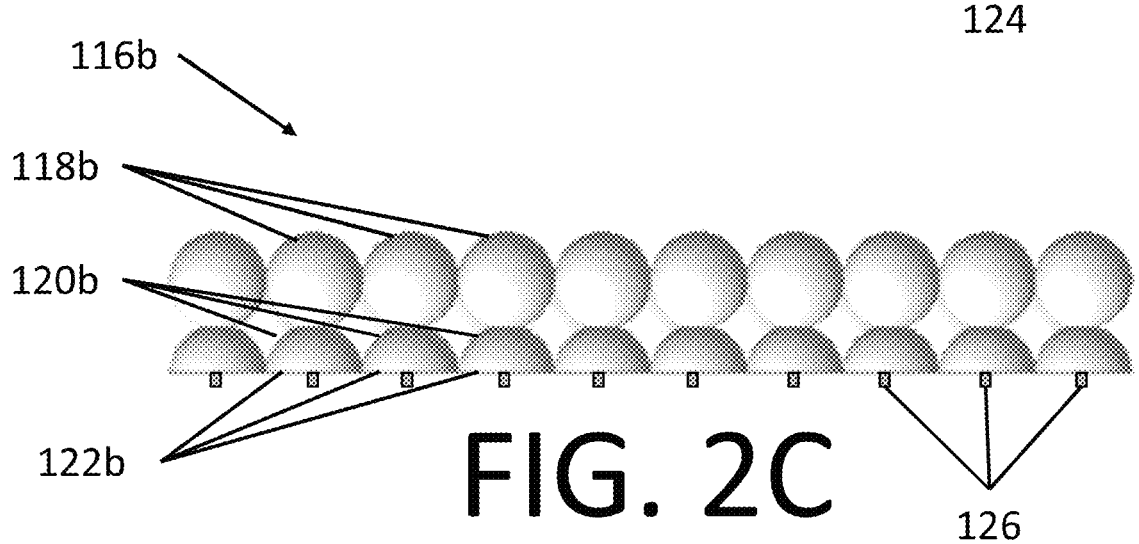

As shown in FIG. 2C, similar to structures 116 and 116a, beaded structure 116b includes a layer of whole beads 118b joined to a layer of planed beads 120b. However, in structure 116b, planed beads 120b each include a stud 124 projecting from planed surface 122b. Studs 124 provide additional surface area and corners to which a flowable adhesive may cling and may be driven into a receiving surface of body 12. Studs 124 may therefore also improve attachment of porous portion 14 to body 12.

Indentations 122a and studs 124 are illustrated as parts of different structures 116a, 116b, but structures according to other arrangements may include both indentations 122 and studs 124. In some such arrangements, each pair of adjacent beads in every row of a layer of beads may include one bead having indentation 122 and another bead having stud 124.

Figure 3A:
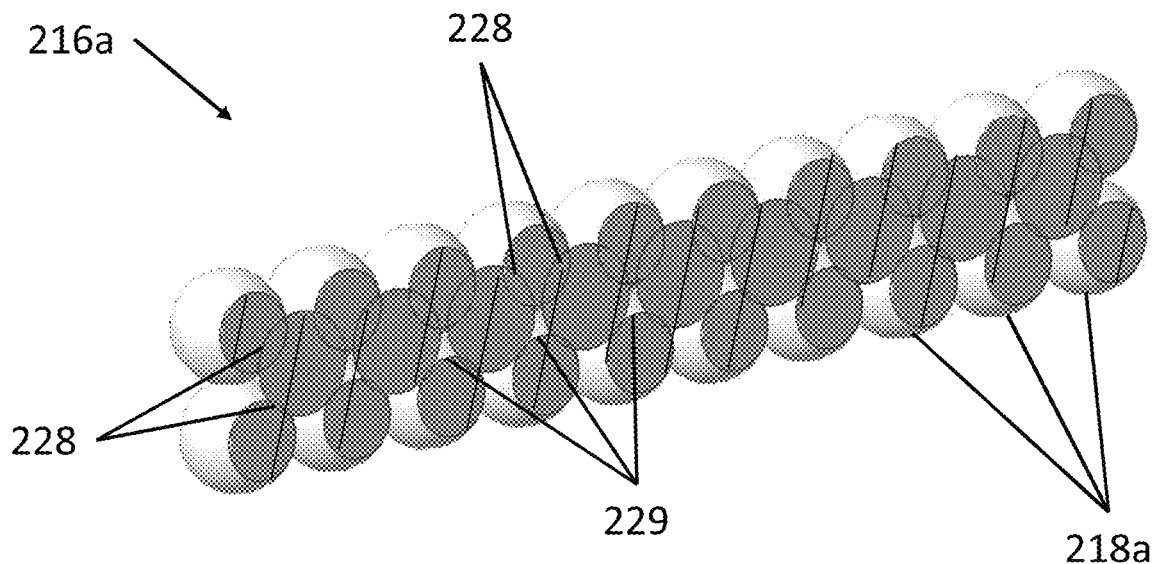
FIGS. 3A and 3B are cross-sections of examples of structures of which the porous portion of FIG. 1C may be made.

Referring now to FIG. 3A, beaded structure 216a formed with theoretical overlaps 228 where partial beads 218a would intersect with neighboring beads if partial beads 218a were whole beads due to the relative proximity of the beads. The three-dimensional shapes, being spheres in the illustrated example, of beads 218a therefore spatially overlap one another. In some examples, the three-dimensional shapes of beads 218a may be regular shapes such as ellipsoids spheres or regular polyhedrons. Beads 218a are therefore integrally formed with one another, which may provide structure 216a with significant strength without need for adhesive or additional joining steps after beads 218a are formed. Moreover, with this configuration, pores 229 defined by partial beads 218a are smaller than pores formed by beads the same size of partial beads 218a if the partial beads were whole beads. Pores 229 are disposed between the beads of beaded structure 216 and thereby define the voids per unit volume of the beaded structure. In this manner, such voids (i.e., pores 229) are external to and disposed between the beads of beaded structure 216 to form a porous structure. Additionally, FIGS. 2A-3B illustrate various embodiments of holeless beads having pores disposed between the holeless beads (e.g., beads 118 and 218).

Figure 3B:
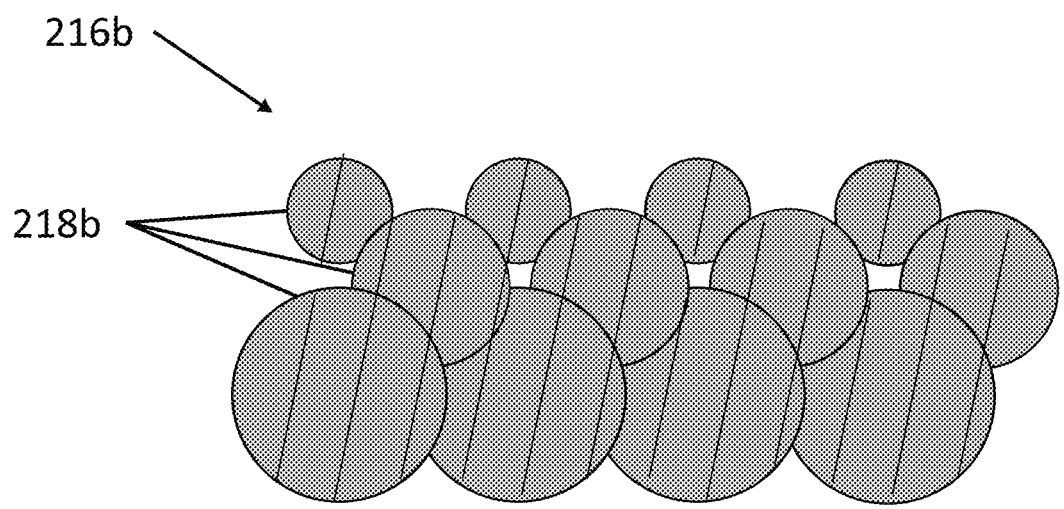

As shown in FIG. 3B, beaded structure 216b is a further variation on any of the foregoing structures 116, 116a, 116b, 216a. Beaded structure 216b includes partial beads 218b of varying size. Partial beads 218b vary from being relatively large at one end, e.g., a lower end relative to an additive manufacturing build substrate, to relatively small at an opposite end, e.g., at a higher end relative to the additive manufacturing substrate, thus providing a gradient of properties such as bead size or pore size within beaded structure 216b. However, the gradient properties may be applied in any direction, and in other arrangements, these properties such as the size of partial beads 218b may vary other than in a continuous gradient. Further, though the beads may intersect one another in a manner similar to beads 218a, such as by the spatial overlap of the shapes of beads 218b in the example illustrated in FIG. 3B, beads in structures according to other examples may vary in size without intersecting one another and without truncating the beads.

Figure 4:
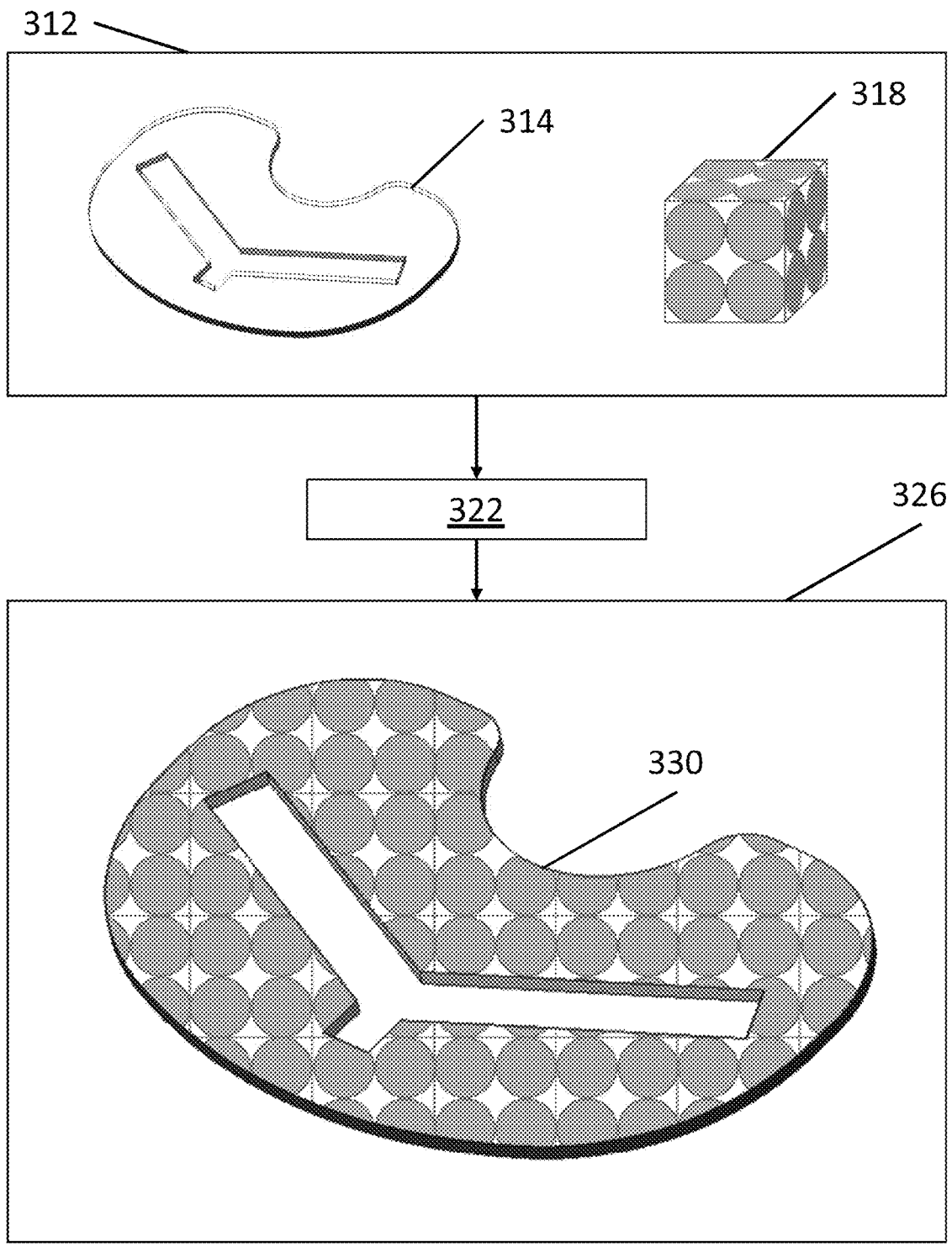
FIG. 4 illustrates a process for deriving a printing plan by which the porous portion of FIG. 1C may be made.

FIG. 4 illustrates a system for generating a set of instructions for additive manufacturing of porous portion 14, which may contain structures 116, 116a, 116b, 216a, 216b according to any of the above-described examples.

Memory 312 is a non-transitory computer readable medium, or multiple such media in cooperation. Part parameters 314 corresponding to aspects of porous portion 14 and populated unit cell 318 are stored on memory 312 as separate pieces of information. Part parameters 314 and populated unit cell 318 may therefore be stored in different locations within memory 312.

Part parameters 314 include at least a CAD volume having a shape corresponding to porous portion 14. The shape of the part includes internal and external surfaces of the part and the relative locations and proportions thereof. Part parameters 314 may also include a size of the part, though in other examples, the shape of the part may be scalable, meaning the size for the part may be a distinct input from part parameters 314.

Populated unit cell 318 is a repeatable three-dimensional structure that includes an arrangement of digitized beads, such as in the form of the beads 118, 118a, 118b, 218a, 218b or any variations thereon described above. Alternatively, populated unit cell 318 may be any portion of an arrangement of such digitized beads.

Memory 312 may be accessed by a processor 322 executing instructions, which may also be stored on memory 312, to initiate an additive manufacturing printing plan from part parameters 314 and populated unit cell 318 and, optionally, additional inputs. Additional inputs may include, for example, a size or scale of the part to be manufactured if the size or scale is not included in part parameters 314. Processor 322 may be a single processor or multiple processors in cooperation.

Executing the instructions causes processor 322 to generate outputs 326 that include or correspond to a digitized porous portion 330 that includes a tessellated plurality of populated unit cells 318. Digitized porous portion 330 may be displayed as a theoretical three-dimensional structure created by repeating populated unit cell 318 throughout the CAD volume of part parameters 314 without any space between populated unit cells 318. Populated unit cells 318 may be truncated at boundaries of the CAD volume of part parameters 314, e.g., by clipping, or altered where necessary at specific locations, but are otherwise repeated in a uniform manner throughout digitized porous portion 330.

Digitized porous portion 330 may contain more information than part parameters 314 and populated unit cell 318 combined. Part parameters 314 and unit cell 318, stored separately, thus may provide the information necessary to generate digitized porous portion 330 while occupying less of memory 312 than the digitized porous portion would.

With digitized porous portion 330 completed, processor 322 may "slice" the digitized porous portion or otherwise reduce digitized porous portion 330 into portions of an additive manufacturing printing plan. Accordingly, processor 322 may execute instructions to generate further instructions, which are among outputs 326, which are a printing plan for an additive manufacturing system. Such printing plan may be stored in a component file, e.g., an .STL or .AMF file, for use by an additive manufacturing system. An additive manufacturing system may then use the component file to execute the printing plan instructions and create porous portion 14 corresponding to the plurality of digitized beads of digitized porous portion 330.

Figure 5:
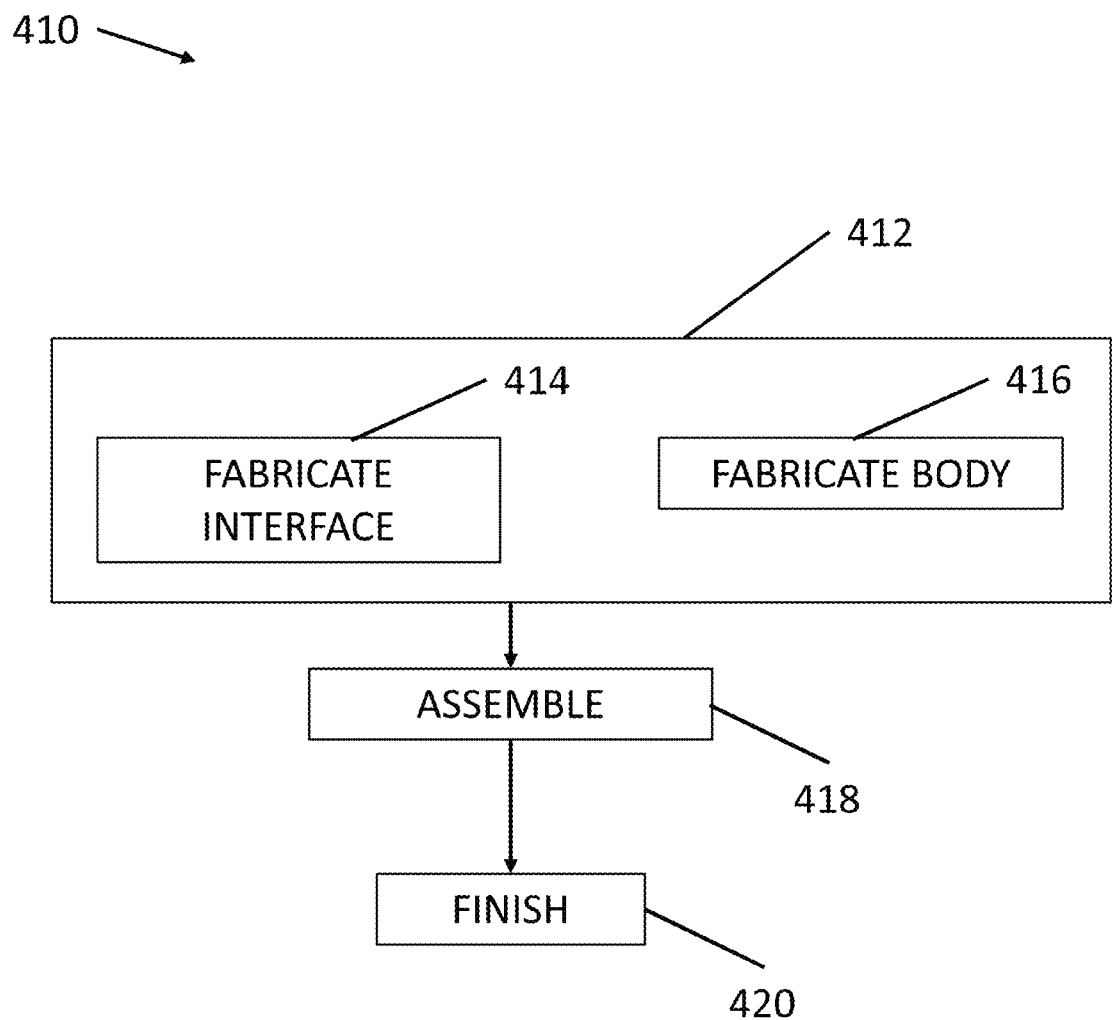
FIG. 5 illustrates a process by which the implant of FIG. 1A may be constructed.

Turning to FIG. 5, process 410 for constructing an implant, such as implant 10, includes fabricating stage 412, followed by an assembly step 418 and a finishing step 420. Fabricating stage 412 includes a porous portion fabricating step 414 in which a porous portion, such as porous portion 14, is fabricated, and an independent body fabricating step 416, in which a body, such as body 12, is fabricated. Either one or both of fabricating steps 414, 416 within fabricating stage 412 may include additive manufacturing according to any of the techniques described above, or any possible combination thereof, or any other process by which a skilled person could fabricate the porous portion and body. Assembly step 418 includes assembling, e.g., via an adhesive, the porous interface and the body into an arrangement generally corresponding to a completed state of the implant. Finishing step 420 includes any necessary processes for bringing the implant to its finished state. Such processes may include, for example, any one or any combination of applying an adhesive if adhesive was not applied in assembly step 418, waiting for adhesive to set, and sintering the implant if either one or both of the porous portion and the body remain in an in-process green state after the assembly step, as well as any post-processing steps such as any one or any combination of heat treatment, machining and polishing.

Figure 6A:
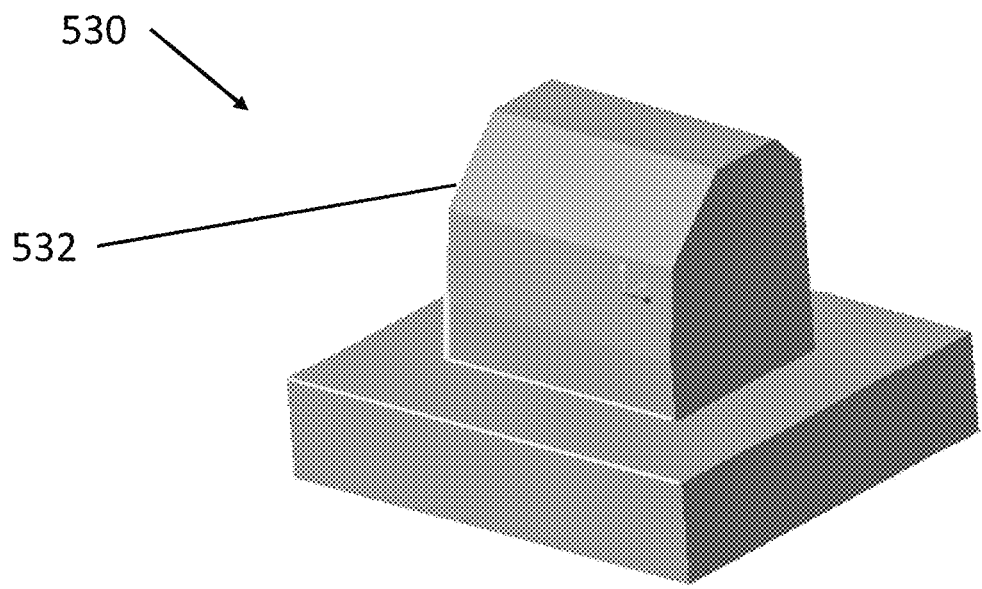
FIG. 6A is a perspective view of a first portion of a metal injection mold.

Stages in an alternative process for constructing an implant are illustrated via of the components and tooling shown in FIGS. 6A-6D. Though the example of FIGS. 6A-6D shows aspects of a process for constructing a distal femoral implant, a similar process may be used to construct other implants or any other piece of hardware including an injection molded part, such as a metal injection molded part, in which another part is embedded. FIG. 6A illustrates a first mold component 530. First mold component 530 includes a supporting surface 532. In the illustrated example, supporting surface 532 includes multiple planar portions and is generally convex, though in other examples, the supporting surface may be entirely planar or planar in other respects than that shown, partially or entirely concave, or any combination of planar, convex, and concave, as feasible and appropriate.

Figure 6B:
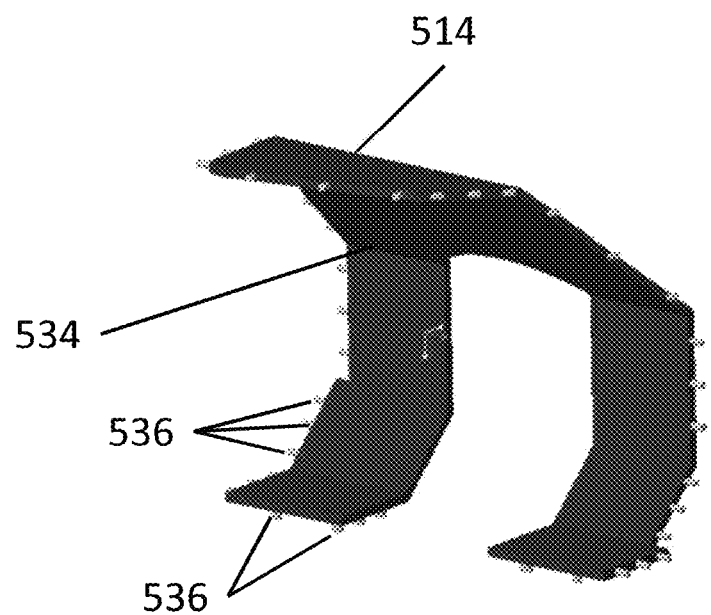
FIG. 6B is a perspective view of an implant porous portion according to another example.

As shown in FIG. 6B, prefabricated component 514, which is a porous portion in the illustrated example may be constructed according to any suitable process, including, for example, any of the additive manufacturing processes described above, including binder jetting. Binder jetting yields a green state part that includes an intended material for the finished part, such as metal, and a binder, e.g., a polymer, wax, latex, or alkali silicate binder, that may be removed in a finishing process, such as sintering. If constructed according to a process that produces a green part, prefabricated component 514 may be either sintered or otherwise finished before placement upon first mold component 530 or placed upon first mold component 530 while prefabricated component 514 remains in a green state. Thus, though prefabricated component 514 is a porous portion in the illustrated example, prefabricated component 514 may include or lack pores in the green state but gain pores while being sintered or otherwise finished.

Prefabricated component 514 includes a support side 534 shaped to enable prefabricated component 514 to rest stably upon supporting surface 532. In the illustrated example, prefabricated component 514 also includes pegs 536 extending from lateral edges of prefabricated component 514 and from a side of prefabricated component 514 opposite from support side 534. Such pegs 536 contribute to secure retention of prefabricated component 514 within a part in which prefabricated component 514 is to be embedded. However, in other examples, pegs 536 may extend from more, fewer, and/or different locations of prefabricated component 514, or may be omitted altogether. In some arrangements, pegs 536 may be formed by additive manufacturing during the fabrication of the rest of prefabricated component 514, which in some other arrangements, the pegs may be joined separately, e.g., by joint welding processes, to the rest of the prefabricated component.

Figure 6C:
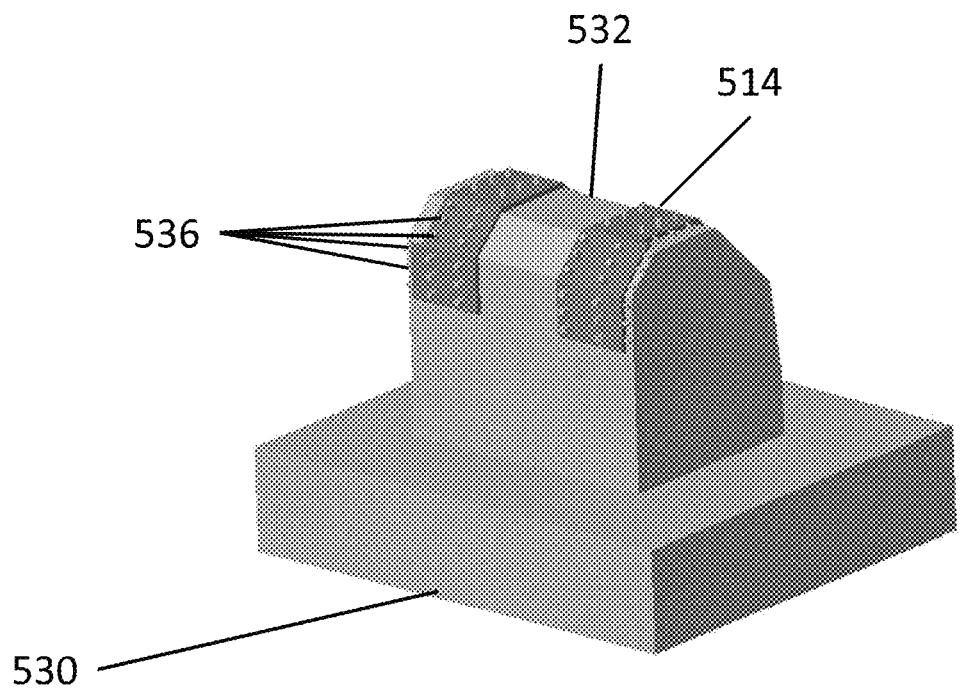
FIG. 6C is a perspective view of the porous portion of FIG. 6B arranged upon the metal injection mold portion of FIG. 6A.

Turning to FIG. 6C, prefabricated component 514 is placed with support side 534 (not visible in FIG. 6C) upon supporting surface 532 of first mold component 530. In the illustrated example, support side 534 conforms to supporting surface 532, though in other examples, supporting surface 532 may otherwise hold prefabricated component 514 at an intended place relative to first mold component 530. In the position of prefabricated component 514 upon first mold component 532 in the stage illustrated in FIG. 6C, pegs 536 are exposed and extend generally away from or parallel to a surface of first mold component 530 and supporting surface 532. In this manner, pegs 536 are received in injected molding material during the molding process.

Figure 6D:
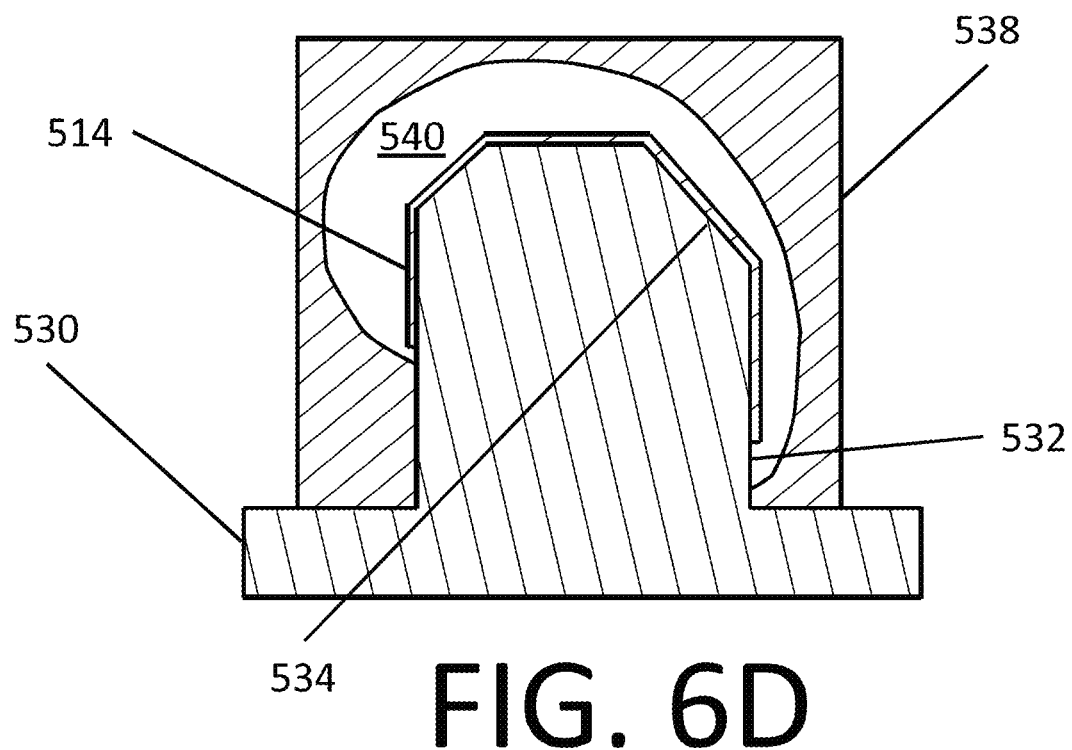
FIG. 6D is a cross-sectional view of a second metal injection mold portion placed upon the arrangement of FIG. 6C.

In FIG. 6D, second mold component 538 is placed on first mold component 530 and over prefabricated component 514 to define cavity 540 in which prefabricated component 514 is enclosed. At least part of supporting surface 532 and the surface opposite support side 534 of prefabricated component 514 define portions bounding cavity 540.

Except for an aperture (not illustrated) through which stock may be injected and disregarding shrinkage, cavity 540 in combination with prefabricated component 514 generally matches a shape of a completed device, which is a distal femoral implant in the illustrated example, or at least exterior contours thereof. Prefabricated component 514 is disposed within cavity 540 at a location corresponding to an intended location within the completed device for prefabricated component 514 to be embedded. Alternatively, prefabricated component 514 may be placed so as to settle into the intended embedded position as material is injected into cavity 540. For example, the feedstock may push prefabricated component 514 from a preliminary position within the empty cavity 540 to the intended embedded position as the feedstock is injected into the cavity. Prefabricated component 514 is retained within cavity 540 at a location such that prefabricated component 514 will be at the intended embedded location when injection is completed by either one or both of first mold component 530 and second mold component 538. Friction and fit between support side 534 and supporting surface 532 may be sufficient to hold prefabricated component 514 at the intended placement. Alternatively, either one or both of first mold component 530 and second mold component 538 may include projections or recesses fitting around prefabricated component 514 to keep prefabricated component 514 in place. In further examples, either one or both of the first mold component 530 and second mold component 538 may additionally or alternatively include any other features for retaining prefabricated component 514 in place during injection, such as, for example, screw holes, posts, or slots.

After arrangement of first mold component 530, prefabricated component 514, and second mold component 538 generally as illustrated in FIG. 6D, material is injected into cavity 540. In the illustrated example, the material injected into cavity 540 would become an implant body in which prefabricated component 514, which is a porous portion in the illustrated example, is embedded. In such example, the implant body has no porosity at all, or has less porosity than a finished state of prefabricated component 514. The injection process and material may be of whatever type is suitable for the completed device. In the example of a distal femoral implant, metal injection molding (MIM) is one example of a suitable injection process and material. Suitable MIM metals include any durable biocompatible metals, such as, for example, titanium, cobalt chrome, or 316 L stainless steel.

MIM yields a green state part including metal, which will become the majority or entirety of the material of the finished part, and a filler or binder, such as plastic, that may be removed by sintering. Where prefabricated component 514 is intended to become a more porous component than the MIM component, the MIM feedstock may include less binder per unit volume than the green state of prefabricated component 514 so that the sintered state of the MIM component has less void per unit volume than the sintered state of prefabricated component 514. MIM parts may be larger in their green state than in their post-sintering state. In such instances, prefabricated component 514 may be in a green state while metal and binder stock is injected into cavity 540, and prefabricated component 514 may have been fabricated with processes and materials such that prefabricated component 514 will shrink during sintering by an amount similar or equal to an amount by which the MIM part in which prefabricated component 514 is embedded will shrink. For example, MIM parts according to some formulations may shrink by about 20% during sintering from the green state to the finished state. Where such MIM formulations are used, prefabricated component 514 may be constructed so as to also shrink by about 20% when sintered. Of course, other formulations are possible whereby the shrinkage of either one or both of the MIM-created portion and the prefabricated component is more or less than about 20%. In some arrangements, the relative porosities of the post-sintering states of the components may be controlled by adjusting the composition of the respective feedstocks used to create the green state components. Filling cavity 540 may therefore produce an overall green state device including a MIM-green state body in which another, distinct green state component (prefabricated component 514) is embedded. In such instance, the two green state components may not be fused to one another at the end of injection. Sintering of such overall green state device will shrink the device by, for example, about 20%, and fuse the two previously green state components thereof together. Where the resulting component is a bone implant, the embedded portion provided by prefabricated component 514 may be more porous than the MIM component after sintering and, possibly, before sintering.

Figure 7:
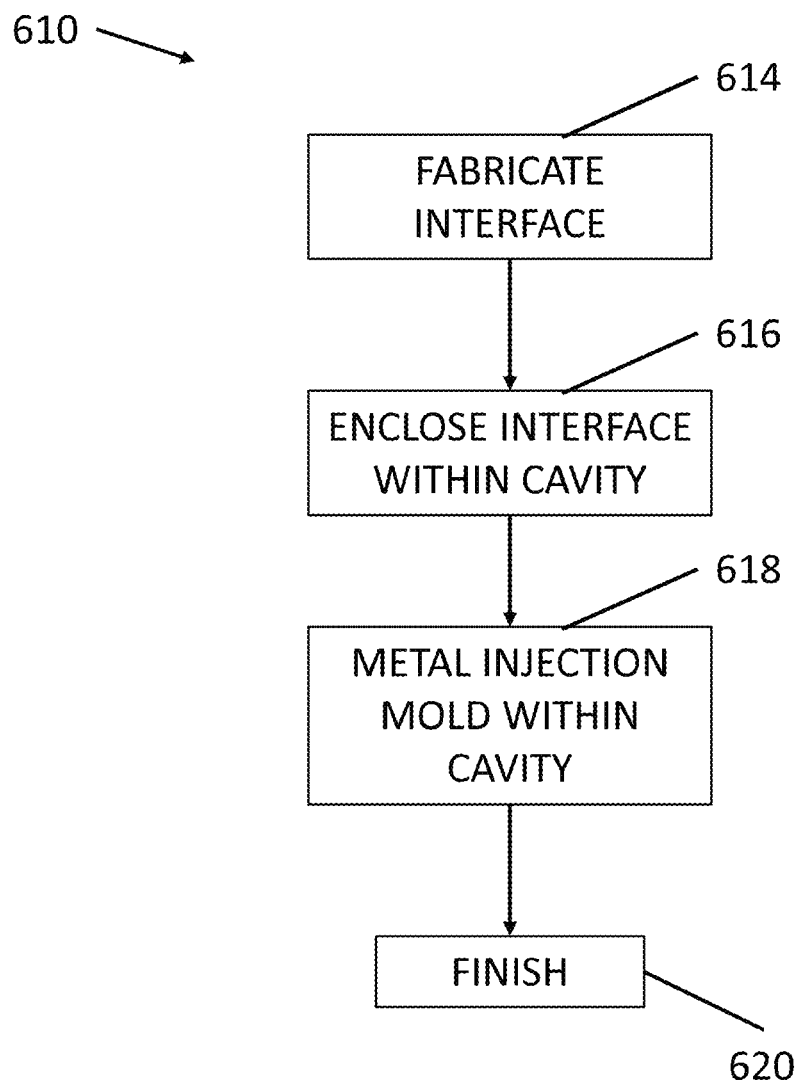
FIG. 7 illustrates a process by which an orthopedic implant including the porous portion of FIG. 6B may be constructed.

FIG. 7 illustrates a process 610 of constructing an implant such as by the stages illustrated in FIGS. 6A-6D. In prefabricating step 614, a component that will become a porous portion is fabricated. The prefabricating step 614 may include any process for fabricating a part that would result in a suitable end product. Additive manufacturing, such as by binder jetting, is one example of a suitable process for prefabricating step 614. The additive manufacturing may include any combination of the features or alternatives described above with regard to the concepts of FIGS. 2A-3B and 6B. After the prefabricating step 614, the porous portion is enclosed in a cavity between two mold components in an enclosing step 616. FIGS. 6C and 6D illustrate two stages in an example of enclosing step 616. An injection step 618 includes injecting MIM stock into the cavity between the two mold components while the porous portion is enclosed in the cavity, such as according to the details described above with regard to FIG. 6D. The stock may have less binder per unit volume than the prefabricated porous portion so as to have less void per unit volume than the porous portion after sintering. An overall green state part results when the injection step 618 is completed. The prefabricated porous portion may be a green state component that either has greater porosity than the rest of the overall green state part or will result in a finished component of greater porosity than the rest of a finished component resulting from the overall green state part. For example, the green state of the prefabricated porous portion may include more binder per unit volume than the green state of the body of the implant so that the post-sintering state of the porous portion will have more void per unit volume than the post-sintering state of the body of the implant. The overall green state part may then be sintered and treated with any other finishing processes necessary at finishing step 620, such as those described previously herein with respect to finishing step 420.

The foregoing concepts may be used in any combination or separately. For example, additive manufacturing may be used to fabricate a porous portion having the unique features of any one or any possible combination of FIGS. 2A-3B. Such additive manufacturing may be binder jetting or any other suitable additive manufacturing process. Additive manufacturing of a porous portion having these unique features may or may not be according to a plan derived entirely or in part from a digitized porous portion 330, created by tessellating a populated unit cell 318 throughout a CAD volume having a shape of a porous portion. A porous portion, which may or may not have any combination of the unique features of FIGS. 2A-3B, and which may or may not be fabricated at least in part in accordance with a digitized portion 330, may be sintered, if applicable, before being integrated with a body portion of an implant. Alternatively, such a porous portion may be fabricated according to a process that does not require sintering, or such a porous portion may be integrated, while in a green state, with a body portion of an implant. A porous portion, which may or may not be a porous portion with any combination of the features described above in this paragraph, may be integrated with a body portion of an implant by adhesion to a prefabricated body portion or by placement in a cavity before the cavity is filled in a metal injection molding process.

Although the concepts herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A method of producing an implant, the method comprising the steps of:
fabricating a first layer of repeated building units;
fabricating a second layer of repeated building units, each of the building units of the second layer intersecting at least one of the building units of the first layer at intersections between the first and the second layers, the first and the second layers together forming a porous section of the implant, at least some of the repeated building units of the first and the second layers define regular shapes, the building units of the first layer or the second layer include holeless beads, wherein at least some pores of the porous section are disposed between the holeless beads; and
attaching the formed porous section to a base section of an implant.

2. The method of claim 1, wherein the building units of the first layer are bound together in a first repeating pattern, and the building units of the second layer are bound together in a second repeating pattern.

3. The method of claim 1, wherein at least some of the building units in the first layer include a flat bottom surface and an indentation extending inwardly from the flat bottom surface.

4. The method of claim 1, wherein at least some of the building units in the first layer include a flat bottom surface and a stud extending outwardly away from the flat bottom surface.

5. The method of claim 1, wherein the first layer fabricating step includes fabricating building units defining a flat bottom surface extending over the entirety of the first layer and thereby a flat bottom surface of the formed porous section upon formation of the formed porous section, and wherein the attaching step includes attaching the formed porous section to a flat surface of the base section of the implant.

6. The method of claim 1, further comprising fabricating a third layer of building units bound together to form additional pores and bound onto the second layer such that the third layer becomes part of the porous section of the implant, wherein the building units in the second layer are different from the building units in the first layer and the building units in the third layer are different from the building units in the first layer and the building units in the second layer.

7. The method of claim 6, wherein the building units in the third layer have a volume that is different than a volume of the building units in the first layer and the building units in the second layer have a volume that is between the volume of the building units in the first layer and the volume of the building units in the third layer.

8. The method of claim 1, wherein the implant is a patient-specific implant.

9. The method of claim 1,
wherein the attaching step includes:
placing the porous section on a supporting region of a first mold component;
positioning a second mold component adjacent the first mold component such that a cavity in the form of the base section of the implant is formed between the first mold component and the second mold component;
while the porous section is placed on the supporting region, filling the cavity with a metal powder mixture; and
compacting the metal powder mixture to provide a solid base formed on the porous section such that the solid base and the porous section form at least a first portion of the implant.

10. The method of claim 9, wherein the porous section comprises studs extending from at least one surface of the porous section, and including positioning the porous section and the second mold component such that the studs extend into the cavity and are over molded by the metal powder mixture upon filling the cavity.

11. The method of claim 9, comprising:
finishing the first portion of the implant to a state wherein the porous section contains more voids per unit volume than the solid base.

12. The method of claim 11, wherein the finishing step includes heating the first portion of the implant to remove a filler from the metal powder mixture.

13. The method of claim 12, wherein the porous section remains in a green state until the finishing step.

14. The method of any claim 9, wherein the supporting region is part of a convex portion of the first mold component.

15. The method of claim 14, wherein the second mold component includes a concave portion, and boundaries of the cavity corresponding to exterior contours of the implant are defined at least partially by the convex portion of the first mold component and the concave portion of the second mold component.

16. The method of claim 1,
wherein each of the steps of fabricating the first layer and fabricating the second layer includes additively manufacturing the first layer and additively manufacturing the second layer, respectively, by binding metal particles with a binder to form a first green state component;
wherein the attaching step includes metal injection molding a metallic mixture material into a second green state component; and
sintering the first green state component and the second green state component to form a first sintered component and a second sintered component, respectively, joined together.

17. The method of claim 16, wherein the first sintered component contains more voids per unit volume than the second sintered component.

18. The method of claim 17, wherein the second sintered component is solid.

19. The method of claim 16, wherein the metal injection molding step of the attaching step includes injecting feedstock into a mold cavity containing the first green state component.

20. The method of claim 1, wherein each of the building units of the first and the second layers defines a sphere except at the intersections.

21. The method of claim 1, wherein the building units of the first layer or the second layer include planed beads joined to the holeless beads, and the planed beads are constructed in a repeating pattern and configured to facilitate attachment of the formed porous section to the base section of the implant.

* * * * *